United States Patent
Godek et al.

(10) Patent No.: US 9,169,237 B1
(45) Date of Patent: Oct. 27, 2015

(54) ANTIPROTOZOAL AMIDINE COMPOUNDS

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: Medi Synergics, LLC, Newington, CT (US)

( * ) Notice: Subject to any disclaimer, the term of this patent is extended or adjusted under 35 U.S.C. 154(b) by 0 days.

(21) Appl. No.: 14/523,278

(22) Filed: Oct. 24, 2014

(51) Int. Cl.
| | |
|---|---|
| *C07D 405/12* | (2006.01) |
| *C07D 307/87* | (2006.01) |
| *A61K 31/155* | (2006.01) |
| *C07D 307/78* | (2006.01) |
| *A61K 31/343* | (2006.01) |
| *A61K 31/443* | (2006.01) |
| *A61K 31/4025* | (2006.01) |
| *A61K 31/404* | (2006.01) |
| *A61K 31/4709* | (2006.01) |
| *A61K 31/4965* | (2006.01) |
| *A61K 31/5377* | (2006.01) |
| *A61K 31/541* | (2006.01) |
| *A61K 31/55* | (2006.01) |
| *A61K 31/4192* | (2006.01) |

(52) U.S. Cl.
CPC ............ *C07D 405/12* (2013.01); *A61K 31/155* (2013.01); *A61K 31/343* (2013.01); *A61K 31/404* (2013.01); *A61K 31/4025* (2013.01); *A61K 31/4192* (2013.01); *A61K 31/443* (2013.01); *A61K 31/4709* (2013.01); *A61K 31/4965* (2013.01); *A61K 31/5377* (2013.01); *A61K 31/541* (2013.01); *A61K 31/55* (2013.01); *C07D 307/78* (2013.01); *C07D 307/87* (2013.01)

(58) Field of Classification Search
CPC ............................ C07D 405/12; C07D 307/87
See application file for complete search history.

(56) References Cited

FOREIGN PATENT DOCUMENTS

WO    WO 2009057974 A2 *    5/2009

* cited by examiner

*Primary Examiner* — Andrew Kosar
*Assistant Examiner* — Matt Mauro

(57) ABSTRACT

The invention is directed to a compound of formula I, as defined herein, or a pharmaceutically acceptable salt thereof; a pharmaceutical composition containing a compound of formula I, a method of treatment of a disorder or condition that may be treated by administration of the compound, the method comprising administering to a mammal in need of such treatment a compound of formula I as described above, and a method of treatment of a disorder or condition selected from the group consisting of Human African Trypanosomiasis (HAT), Chagas disease, malaria and Leishmaniasis, the method comprising administering to a mammal, including a human, in need of such treatment a compound of formula I as described above.

15 Claims, No Drawings

ANTIPROTOZOAL AMIDINE COMPOUNDS

This application claims the benefit of U.S. Provisional application Ser. No. 61/899,181 filed on Nov. 2, 2013.

BACKGROUND OF THE INVENTION

This invention is directed to compounds of the formula I described herein, to a pharmaceutical composition comprising such compounds and to methods of preventing or treating disorders or conditions that may be treated by administration of such compounds to a mammal in need, including humans. In particular, the compounds of the current invention are potentially useful for treating certain protozoal infections including, for example, human African trypanosomiasis (HAT) and Chagas disease.

Human African Trypanosomiasis (HAT) is a disease spread by a parasitic organism, *trypanosoma brucei*, which is transmitted to humans primarily via bites from the tsetse fly—transmission may also occur via blood transfusion or in utero exposure of a fetus from an infected mother via the placenta. It is often referred to as "sleeping sickness" because of the symptoms that develop in patients who have progressed to the advanced, or Stage 2, level of infection wherein the parasite has passed the blood brain barrier (BBB) exposing the central nervous system (CNS) of the victim to further infection by the parasite. Left untreated, this latter stage of the disease is typically fatal. Jacobs and Ding, *Annual Reports in Medicinal Chemistry*, 2010-45, 277-294; Chapter 50 of *Goodman and Gilman's, The Pharmacological Basis of Therapeutics*, 12$^{th}$ Ed., 2011, 1419-1441.

The disease is found in two forms, depending on the parasite sub-species involved, either *Trypanosoma brucei gambiense* or *Trypanosoma brucei rhodesiense*. Humans are the primary host for *Trypanosoma brucei gambiense*, whereas wild game animals and cattle are the primary target of *T. b. rhodesiense*. *T. b. gambiense* is found in central and western Africa and causes a chronic condition that can remain in a passive phase for months or years before symptoms emerge. *T. b. rhodesiense* is found in southern and eastern Africa; symptoms of infection by *T. b. rhodesiense* generally emerge in a few weeks and are more virulent and faster developing than *T. b. gambiense*.

While approximately one-half million inhabitants of sub-Saharan Africa are potentially infected each year by the hemolymphatic, Stage 1, form of HAT. The number of HAT cases has been diminishing, with the WHO estimating an annual mortality of 10,000 (see P. P. Simarro, et al, *International Journal of Health Geographics*, 2010, 9, 57). However, this trend has varied over the years and, with few efficacious and cost effective preventative measures being consistently used, the number of cases would quickly rebound. Symptoms include fever, headaches, joint pains and itching, as well as severe swelling of lymph nodes. Chronically, HAT can produce more extensive symptoms including anemia, endocrine, cardiac and kidney dysfunctions.

The drugs that are available act directly on the invasive protozoa in the bloodstream; penetration of the blood-brain barrier (BBB) has limited the use of some of these drugs to treatment of the hemolymphatic, first stage of HAT. These include suramin, developed in the 1920's and primarily used for Stage 1 *T. b. rhodesiense* HAT; pentamidine, discovered in 1940, which requires multiple intramuscular (i.m.) injections and is only effective for Stage 1 HAT; melarsoprol (identified in 1949) which also requires multiple, painful daily injections and is highly toxic, often used for the most severely ill Stage 2 patients; and eflornithine, a drug developed in 1981 which requires slow i.v. infusions over a two-week period to ensure sufficient CNS exposure to treat *T. b. gambiense*-induced Stage 2 HAT. A nifurtimox-eflornithine combination therapy (NECT) was created in 2009; it appears to be better tolerated for Stage 2 HAT patients (see Nok, *Expert Opinion in Pharmacotherapy*, 2005, 6(15), 2645-2653).

Of growing concern in recent years is the issue of cross-resistance to some of these medications. This has been observed with pentamidine and arsenicals like melarsoprol. (See de Koning, *Trends in Parasitology*, 2008, 24(8), 345-349).

Interestingly, the organism that is responsible for HAT, *T. brucei*, is related to other parasitic species that can cause severely debilitating diseases in humans and animals. Chagas disease, caused by the related parasite *T. cruzi*, is prevalent in South America, affecting up to 10 million individuals and has also been detected in cattle; fatalities from Chagas are estimated to be about 21,000 per year. Leishmaniases, in their various manifestations—cutaneous Leishmaniasis (via *L. major, L. mexicana, L. aethiopica, L. tropica*), mucocutaneous leishmaniasis (*L. braziliensis*) and visceral leishmaniasis (*L. donovani/infantum*) are estimated to affect nearly 2 million people on four continents. It is quite possible that any new treatment for HAT which targets the *T. brucei* parasite could have sufficient efficacy against these related parasitic species and, therefore would be a valuable improvement in antiparasitic therapy. (See Silva, et al, *Biochemical Pharmacology*, 2007, 73, 1939-1946).

One of the most commonly used HAT treatments for Stage 1 is pentamidine. This diamidine compound has been extensively studied with respect to structure-activity relative to the replacement of its 1,5-dioxopentyl section by a variety of aryl and heteroaryl rings (See, e.g., R. R. Tidwell, et al, in *Journal of Medicinal Chemistry*, 2006, 49, 5324; *Journal of Medicinal Chemistry*, 2007, 50, 2468; *Journal of Medicinal Chemistry*, 2008, 51, 6923; *Journal of Medicinal Chemistry*, 2009, 52, 5763; *Journal of Medicinal Chemistry*, 2010, 53, 254). Little research has been done to enhance pentamidine's brain concentration through the incorporation into the molecule of CNS-penetration enhancing groups, such as those found in some effective antipsychotic and antidepressant drugs currently on the market.

Malaria is another infectious disease caused by parasitic protozoa. Transmitted via a bite from an infected female *Anopheles* mosquito into a human or animal's circulatory system, they travel to the liver to mature and reproduce. Malaria causes symptoms that typically include fever and headache, which in severe cases can progress to coma or death. The disease is widespread in tropical and subtropical regions in a broad band around the equator, including much of Sub-Saharan Africa, Asia, and the Americas. Five species of *Plasmodium* can infect and be transmitted by humans; the vast majority of deaths are caused by *P. falciparum* and *P. vivax*.

Symptoms of falciparium malaria appear 9-30 days after infection (Bartoloni A, Zammarchi L (2012). "Clinical aspects of uncomplicated and severe malaria". *Mediterranean Journal of Hematology and Infectious Diseases* 4 (1): e2012026). Individuals with cerebral malaria frequently exhibit neurological symptoms, including abnormal posturing, nystagmus, conjugate gaze palsy (failure of the eyes to turn together in the same direction), opisthotonus, seizures or coma. Serious complications of malaria include the development of respiratory distress, which occurs in up to 25% of adults and 40% of children with severe *P. falciparum* malaria. Infection with *P. falciparum* may result in cerebral malaria, a form of severe malaria that involves encephalopathy.

The World Health Organization (WHO) estimated that in 2010, there were 219 million documented cases of malaria and 1.24 million deaths (Murray C J, Rosenfeld L C, Lim S S, Andrews K G, Foreman K J, Haring D, Fullman N, Naghavi M, Lozano R, Lopez A D (2012). "Global malaria mortality between 1980 and 2010: A systematic analysis". *Lancet* 379 (9814): 413-31). The majority of cases (65%) occur in children under 15 years old and maternal malaria is associated with up to 200,000 estimated infant deaths yearly (Hartman T K, Rogerson S J, Fischer P R (2010). "The impact of maternal malaria on newborns". *Annals of Tropical Paediatrics* 30 (4): 271-82).

Several medications are available to prevent malaria in travelers to malaria-endemic countries. Severe malaria is treated with intravenous or intramuscular quinine or, since the mid-2000s, the artemisinin derivative artesunate, which is superior to quinine in both children and adults and is given in combination with a second anti-malarial such as mefloquine. Resistance has developed to several antimalarial drugs; for example, chloroquine-resistant *P. falciparum* has spread to most malarial areas, and emerging resistance to artemisinin has become a problem in some parts of Southeast Asia.

Uncomplicated malaria may be treated with oral medications. The most effective treatment for *P. falciparum* infection is the use of artemisinins in combination with other antimalarials known as artemisinin-combination therapy (or ACT), which decreases resistance to any single drug component (Kokwaro G (2009). "Ongoing challenges in the management of malaria". *Malaria Journal* 8 (Suppl. 1): S2). These additional antimalarials include: amodiaquine, lumefantrine, mefloquine or sulfadoxine/pyrimethamine. Another recommended combination is dihydroartemisinin and piperaquine (WHO 2010, pp. 75-86; Kokwaro G (2009) "Ongoing challenges in the management of malaria". *Malaria Journal* 8 (Suppl. 1): S2).

There are a number of drugs that can help prevent malaria while travelling in areas where it exists. Most of these drugs are also sometimes used in treatment. Chloroquine may be used where the parasite is still sensitive (Jacquerioz F A, Croft A M (2009). "Drugs for preventing malaria in travelers". In Jacquerioz F A. *Cochrane Database of Systematic Reviews (Online)* (4): CD006491). Because most *Plasmodium* is resistant to one or more medications, one of three medications—mefloquine, doxycycline or the combination of atovaquone and proguanil hydrochloride—is frequently needed. Doxycycline and the atovaquone and proguanil combination are the best tolerated; mefloquine is associated with death, suicide, and neurological and psychiatric symptoms. The protective effect does not begin immediately, and people visiting areas where malaria exists usually start taking the drugs one to two weeks before arriving and continue taking them for four weeks after leaving (with the exception of atovaquone/proguanil, which only needs to be started two days before and continued for seven days afterward) (Freedman DO (2008). "Clinical practice. Malaria prevention in short-term travelers". *New England Journal of Medicine* 359 (6): 603-12.

Aromatic amidine compounds have been reported to have efficacy in the treatment of human and animal disorders like giardiasis (U.S. Pat. No. 4,963,589, issued Oct. 16, 1990), *pneumocystis carinii* pneumonia (U.S. Pat. No. 4,933,347, issued Jun. 12, 1990), *leishmania donovani* (U.S. Pat. No. 5,786,383, issued Jul. 28, 1998), *plasmodium falciparum* malaria (U.S. Pat. No. 5,206,236, issued Apr. 27, 1993), as well as their use as anticoagulants (U.S. Pat. No. 5,866,577, issued Feb. 2, 1999), antiproliferative agents (U.S. Pat. No. 6,699,862, issued Mar. 2, 2004) and antihistamine substances (U.S. Pat. No. 4,748,165, issued May 31, 1988)

SUMMARY OF THE INVENTION

This invention is directed to compounds of the formula I:

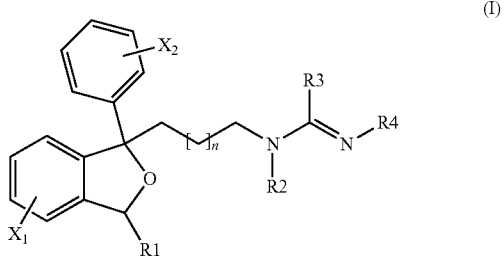

or the pharmaceutically acceptable salt(s) thereof, wherein:
$X_1$ is selected from the group consisting of H, ($C_1$-$C_4$) alkyl, ($C_1$-$C_4$)-alkoxyl, $CF_3$, F, Cl, Br, I, CN.
$X_2$ is H, I, Br, Cl, or F;
n is zero, one or two;
R1 is H, methyl, or dimethyl;
R2 is H, ($C_1$-$C_6$)-alkyl;
R3 is H, ($C_1$-$C_6$)-alkyl, ($C_3$-$C_{12}$)-cycloalkyl (optionally containing a S or O atom), aryl (optionally substituted by $X_3$), or (($C_1$-$C_6$)-alkyl)-aryl;
R4 is ($C_1$-$C_6$)-alkyl, aryl (optionally substituted by $X_4$); or
R3 and R4 together with the carbon and nitrogen atoms to which they are attached form a 5-12 member mono- or bi-cyclic ring system, (said ring system containing up to two additional heteroatoms selected from N, O or S, and said ring optionally substituted at available positions by one or more groups from a list which includes ($C_1$-$C_6$)-alkyl, ($C_1$-$C_6$)-alkoxyl and aryl) including, e.g., 4,5-dihydro-imidazol-2-yl; 1,3,4-oxadiazol-2-yl, 1,2,4-triazol-3-yl, tetrazole-5-yl, 3,4-dihydro-quinolin-2-yl; 3,4-dihydro-2H-pyrrol-5-yl; 2,3,4,5-tetrahydro-pyridin-6-yl; 1,2,3,6-tetrahydro-pyrazin-2-yl; 3,6-dihydro-2H-1,4-oxazin-5-yl; 1,2-dihydro-quinoxalin-3-yl; 4,5-dihydro-3H-2-benzazepin-1-yl; and 2,5-dihydro-1H-3-benzazepin-4-yl;
$X_3$ and $X_4$ are independently selected from the list consisting of: H, F, Cl, Br, I, CN, ($C_1$-$C_6$)-alkyl, ($C_3$-$C_{12}$)-cycloalkyl, $CF_3$, $C_2F_5$, $OCF_3$, O—($C_1$-$C_6$)-alkyl, O—($C_1$-$C_6$)-alkoxyl, OH, $NO_2$, $NH_2$, NHR7 and NR7R8; wherein R7 and R8 are independently selected from the list including ($C_1$-$C_6$)-alkyl, ($C_3$-$C_{12}$)-cycloalkyl and phenyl, or wherein R7 and R8 together with the N to which they are attached form a 4-12 membered mono- or bi-cyclic ring.

The invention is also directed to a pharmaceutical composition for treating, for example, a disorder or condition (e.g., human African trypanosomiasis, Chagas disease) in a mammal, including a human, that may be treated by comprising administering to a mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the preceding paragraph (e.g. human African trypanosomiasis, Chagas disease), the method comprising administering to said mammal in need of such treatment an amount of a compound of formula I as described above that is effective in treating such disorder or condition.

The invention also relates to the use of a compound of the formula I, or a pharmaceutically acceptable salt thereof, in the manufacture of a medicament for the treatment of a disorder or condition, the treatment of which can be effected or facilitated by administration of an effective amount of the medicament to a mammal, including a human, in need of such treatment.

Preferred embodiments of the present invention include the compounds of formula I in which:
(A) R1 is hydrogen, R2 is methyl, R4 is hydrogen;
n is one; and
R3 is ($C_1$-$C_6$)alkyl.
(B) R1 is hydrogen, R2 is methyl, R4 is hydrogen;
n is one; and
R3 is aryl (optionally substituted by $X_3$).
(C) R1 is hydrogen, R2 is methyl;
n is one; and
R3 and R4, taken together with the carbon and nitrogen atoms to which they are attached, respectively, form a 5-12 member mono- or bi-cyclic ring system as previously defined.

The most preferred embodiment of the present invention includes the compounds of formula I in which:
(A) X1 is CN and X2 is fluoro, n is one;
R1 is hydrogen, R2 is methyl, R4 is hydrogen; and
R3 is phenyl.
(B) X1 is CN and X2 is fluoro, n is one;
R1 is hydrogen, R2 is methyl, R4 is hydrogen; and
R3 is ($C_1$-$C_6$)alkyl.

Preferred compounds of formula I in accordance with the present invention include the following:
1-(4-fluorophenyl)-1-{3-[methyl(3,4,5,6-tetrahydropyridin-2-yl)amino]propyl}-1,3-dihydro-2-benzofuran-5-carbonitrile;
1-{3-[3,4-dihydro-2H-pyrrol-5-yl(methyl)amino]propyl}-1-(4-fluorophenyl)-1,3-dihydro-2-benzofuran-5-carbonitrile;
1-{3-[3H-indol-2-yl(methyl)amino]propyl}-1-(4-fluorophenyl)-1,3-dihydro-2-benzo-furan-5-carbonitrile;
1-{3-[3,4-dihydroquinolin-2-yl(methyl)amino]propyl}-1-(4-fluorophenyl)-1,3-dihydro-2-benzofuran-5-carbonitrile;
1-{3-[3,4,4a,5,6,7,8,8a-octahydroquinolin-2-yl(methyl)amino]propyl}-1-(4-fluorophenyl)-1,3-dihydro-2-benzofuran-5-carbonitrile;
1-{3-[methyl(4-methyl-3,4,5,6-tetrahydropyrazin-2-yl)amino]propyl}-1-(4-fluorophenyl)-1,3-dihydro-2-benzofuran-5-carbonitrile;
1-{3-[5,6-dihydro-2H-1,4-oxazin-3-yl(methyl)amino]propyl}-1-(4-fluorophenyl)-1,3-dihydro-2-benzofuran-5-carbonitrile;
1-{3-[5,6-dihydro-2H-1,4-thiazin-3-yl(methyl)amino]propyl}-1-(4-fluorophenyl)-1,3-dihydro-2-benzofuran-5-carbonitrile;
1-{3-[methyl(2,3,6,7-tetrahydro-1,4-oxazepin-5-yl)amino]propyl}-1-(4-fluorophenyl)-1,3-dihydro-2-benzofuran-5-carbonitrile;
1-{3-[methyl(3,4,5,6-tetrahydro-2H-azepin-7-yl)amino]propyl}-1-(4-fluorophenyl)-1,3-dihydro-2-benzofuran-5-carbonitrile;
1-{3-[(2,2-dimethyl-3,4-dihydro-2H-pyrrol-5-yl)(methyl)amino]propyl}-1-(4-fluorophenyl)-1,3-dihydro-2-benzofuran-5-carbonitrile;
1-{3-[methyl(4H-1,2,3-triazol-5-yl)amino]propyl}-1-(4-fluorophenyl)-1,3-dihydro-2-benzofuran-5-carbonitrile;
N-3-(5-cyano-1-(4-fluorophenyl)-1,3-dihydro-2-benzofuran-1-yl)-propyl]-N-methyl-propanimidamide;
N-3-(5-cyano-1-(4-fluorophenyl)-1,3-dihydro-2-benzofuran-1-yl)-propyl]-N-methyl-cyclopropanecarboximidamide
N-3-(5-cyano-1-(4-fluorophenyl)-1,3-dihydro-2-benzofuran-1-yl)-propyl]-N-methyl-cyclohexanecarboximidamide
N-3-(5-cyano-1-(4-fluorophenyl)-1,3-dihydro-2-benzofuran-1-yl)-propyl]-N-methyl-tetrahydro-2H-pyran-4-carboximidamide;
N-3-(5-cyano-1-(4-fluorophenyl)-1,3-dihydro-2-benzofuran-1-yl)-propyl]-4-chloro-N-methylbenzenecarboximidamide;
N-3-(5-cyano-1-(4-fluorophenyl)-1,3-dihydro-2-benzofuran-1-yl)-propyl]-3,4-difluoro-N-methylbenzenecarboximidamide;
N-3-(5-cyano-1-(4-fluorophenyl)-1,3-dihydro-2-benzofuran-1-yl)-propyl]-4-methoxy-N-methylbenzenecarboximidamide;
N-3-(5-cyano-1-(4-fluorophenyl)-1,3-dihydro-2-benzofuran-1-yl)-propyl]-N-methyl-naphthalene-2-carboximidamide;
N-3-(5-cyano-1-(4-fluorophenyl)-1,3-dihydro-2-benzofuran-1-yl)-propyl]-N-methyl-naphthalene-1-carboximidamide;
(1Z)—N-3-(5-cyano-1-(4-fluorophenyl)-1,3-dihydro-2-benzofuran-1-yl)-propyl]-N,N'-dimethylethanimidamide;
(1E)-N-3-(5-cyano-1-(4-fluorophenyl)-1,3-dihydro-2-benzofuran-1-yl)-propyl]-N,N'-dimethylethanimidamide;
(1Z)—N-3-(5-cyano-1-(4-fluorophenyl)-1,3-dihydro-2-benzofuran-1-yl)-propyl]-N,N',2-trimethylpropanimidamide;
(1Z)—N-3-(5-cyano-1-(4-fluorophenyl)-1,3-dihydro-2-benzofuran-1-yl)-propyl]-N,N'-dimethyl-3-phenylpropanimidamide;
N-3-(5-cyano-1-(4-fluorophenyl)-1,3-dihydro-2-benzofuran-1-yl)-propyl]-N,N'-dimethyl-benzenecarboximidamide;
1-{-3-[4,5-dihydro-1H-3-benzazepin-2-yl-amino]propyl}-1-(4-fluorophenyl)-1,3-dihydro-2-benzofuran-5-carbonitrile;
1-{3-[4,5-dihydro-3H-2-benzazepin-1-yl-amino]propyl}-1-(4-fluorophenyl)-1,3-dihydro-2-benzofuran-5-carbonitrile; and
1-{3-[4-methyl-3,4-dihydroquinoxalin-2-yl(methyl)amino]propyl}-1-(4-fluorophenyl)-1,3-dihydro-2-benzofuran-5-carbonitrile.

The most preferred compounds of the invention include:
N-{3-[5-cyano-1-(4-fluorophenyl)-1,3-dihydro-2-benzofuran-1-yl]propyl}-N-methyl-ethanimidamide;
N-{3-[5-cyano-1-(4-fluorophenyl)-1,3-dihydro-2-benzofuran-1-yl]propyl}-N-methyl-phenylmethanimidamide;

A preferred use for compounds of formula I is in the treatment of human African trypanosomiasis (HAT). Other preferred uses for the compounds of formula I are in the treatment of Chagas disease, malaria and in the treatment of Leishmaniasis.

DETAILED DESCRIPTION OF THE INVENTION

The compounds of formula I may be prepared as described in the following reaction schemes and discussions. Unless otherwise indicated, n, $X_1$, $X_2$, R1, R2, R3, R4, R5 and structural formulae II, III, IV and V in the reaction schemes and discussion that follow are as defined above.

Scheme 1

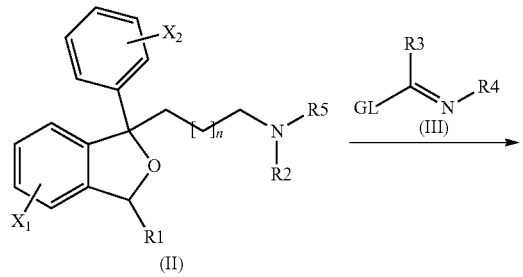

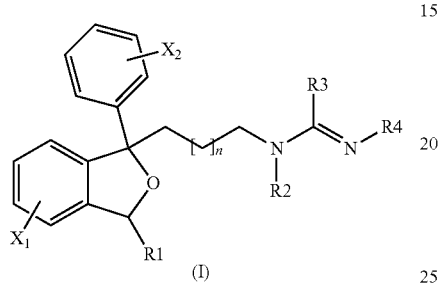

According to Scheme 1, compounds of the general formula II, wherein R5 is hydrogen, can be converted to the compounds of general formula I, by reaction with a compound of general formula III:

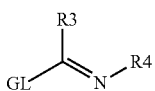

wherein R3 and R4 are as described above and GL is a leaving group, e.g., Cl, $OR_6$, $SR_6$, etc., and wherein R6 is $C_1$-$C_6$ alkyl. Formation of the resultant amidine group is well precedented in the chemical and patent literature. One excellent general reference, for example, is from R. L. Shriner and F. W. Neumann, "The Chemistry of the Amidines", 1944, 35:351-425. Other references include, for example, Moreau, et al, European Journal of Medicinal Chemistry, 1977, 12(4):365-369; Exner, et al, Journal of Molecular Structure, 1988, 178:147-159.

Scheme 2

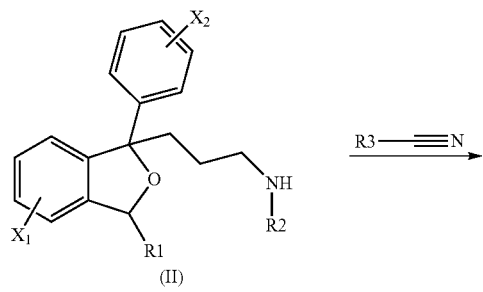

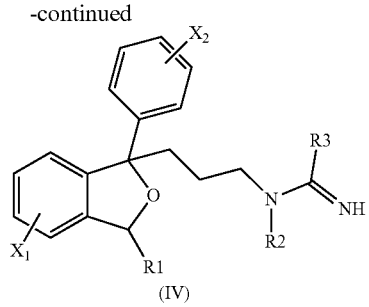

An alternative method, as shown in Scheme 2, involves the reaction of a compound of general formula II, wherein R5 is hydrogen, with a nitrile of general formula V:

wherein R3 is as defined previously, to produce a compound of general formula IV (i.e., formula I wherein R4 is hydrogen). Using this procedure, $X_1$ is generally not equal to cyano (i.e., CN). Conditions for this procedure generally require the presence of an alcohol, preferably methanol or ethanol, and an anhydrous mineral acid, preferably hydrochloric acid, to be combined with the nitrile V and reacted within a temperature range of about 0° C. to about the boiling point of the alcohol employed, preferably at about 80° C. for ethanol, and at a pressure of about one to three atmospheres, preferably at atmospheric pressure, to generate an intermediate alkyl imidate. The intermediate imidate may then be isolated and purified, or reacted directly with the compound of general formula II in a reaction inert solvent such as toluene, 1,4-dioxane and the like, and stirred for up to 24 hr at a temperature in the range of about 0° C. to about 100° C. This process has been discussed in a number of literature sources, including those by Patai, "The Chemistry of Amidines and Imidates", Wiley, New York, 1975, pp. 385-489; R. Roger and D. Neilson, Chemical Reviews, 1961, 61(2): 179-211.

The starting materials for this process, compounds of the general formula II, are readily available using procedures described in the chemical and patent literature. For example, the compound of formula II, wherein n=1, R2=CH3, R5=CH3, R1=H, $X_2$ is 4-fluoro and the CN group is attached to the 5-position of the benzofuran ring has been commercially available as the antidepressant citalopram (in racemic form) and as the antidepressant escitalopram (as the single, (S)-isomer). Procedures for the syntheses of these compounds are also available in the literature (e.g., see M. Pitts, Tetrahedron, 2006, 62, 4705-4708; N. Periyandi, et al, PCT Int. Appl., (2006), WO-2006021971; T. Ikemoto and Y. Watanabe, PCT Int. Appl., (2005), WO-2005082842; H. Ahmadian and H. Petersen, PCT Int. Appl., (2003), WO-2003051861; H. Petersen, PCT Int. Appl. (2001), WO-2001068631; L. Dall'Asta, et al, PCT Int. Appl., (2000), WO-2000023431).

The starting material of general formula II, wherein R5 is hydrogen can be prepared from the preceding compounds by a mono-demethylation reaction. The process is also well precedented in the chemical literature and has been used to synthesize the major des-methyl metabolite of the above-mentioned citalopram and escitalopram. See, for example, C. Jin, et al (Synthetic Communications, 2007, 37, 901-908).

The compounds of the general formula III used in Scheme I above may be available commercially or can be prepared by methods disclosed in the chemical literature and known to one skilled in the art of organic chemistry. For example, see the Shriner paper above, and the specific references therein. For a more recent review of amidine chemistry, see M. S. dos Santos, et al, "Synthetic Approaches to Amidines", Quimica Nova, 2006, 29(6):1301-1306.

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring.

Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl (tetralinyl), indenyl, and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen, and sulfur. Examples of preferred heteroaryl groups include benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The compounds of formula I may also exist in the form of cis- or trans-isomers with respect to configuration on the furan ring of formula I. Such cis- and trans-isomers are also considered to be within the scope of the present invention, The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2H$, $^3H$, $^{11}C$, $^{13}C$, $^{14}C$, $^{13}N$, $^{15}N$, $^{17}O$, $^{18}O$, $^{35}S$, $^{31}P$, $^{32}P$, $^{31}P$, $^{18}F$ and $^{37}Cl$, respectively. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof, and pharmaceutically acceptable salts of said compounds, or of said prodrugs which contain the aforementioned isotopes and/or other isotopes of other atoms are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., HAT) is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above (e.g., HAT) in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by a compound, composition and method of this invention include: human African trypanosomiasis (HAT), Chagas disease, Leishmaniasis, giardiasis, *pneumocystis carinii* pneumonia or malaria.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:

bm: broad multiplet (NMR)
bs: broad singlet (NMR)
d: doublet (NMR)
dd: doublet of doublets (NMR)
d.e.: diatomaceous earth, filtering agent calcd.: calculated value
equiv: equivalent
J: coupling constant (NMR)
HPLC: high pressure liquid chromatography
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton (i.e., $^1H$) NMR spectra are reported in parts per million (ppm) relative to the singlet of $CDCl_3$ at 7.24 ppm.

Conditions for High Pressure Liquid Chromatography—Mass Spectrometry (HPLC-MS) Analysis:

Column: Zorbax RRHD Eclipse Plus (Agilent) $C_{18}$, 1.9 micron, 50 mm×2.1 mm

Eluent I.
  A: Acetonitrile-$H_2O$=5:95, 20 mM $HCOONH_4$/$NH_4OH$ buffer, pH 7.4
  B: Acetonitrile-$H_2O$=80:20, 20 mM $HCOONH_4$/$NH_4OH$ buffer, pH 7.4

Eluent II.
  A: $H_2O$ with 0.1% TFA, pH 2.2
  B: Acetonitrile with 0.1% TFA, pH 2.2

Gradient program: adjusted according to the compound properties; typically, start: 0% B to 100% B in 1 minute, 0.8 minute isocratic B.

Column Temp.: 40° C.
Flow Rate: 0.6 mL/min
Sample Conc.: ca. 1 mg/mL
Sample Solvent: Acetonitrile
Injection: 0.5 μL
Detection wavelength: 220 nm Mass Spectrum (MS) Conditions:
  Measured Mass Range: 100-750 Daltons
  Scan Time: 0.2 s
  Ion mode: ES±
  Cone Voltage: 20 V
  Capillary Voltage: 3V
  Source temp.: 140° C.
  Desolvation temp.: 450° C.
  Desolvation gas: 450 L/h
  Cone gas: 60 L/h

EXPERIMENTAL SECTION

Preparation 1

1-[3-(methylamino)propyl]-1-(4-fluorophenyl)-1,3-dihydro-2-benzofuran-5-carbonitrile

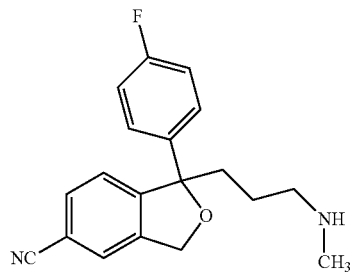 [SMILES: CNCCCC1(c2ccc(F)cc2)OCc2cc(C#N)ccc21]

The title compound was prepared according to the method of C. Jin, et al (*Synthetic Communications*, 2007, 37, 901-908). Thus, citalopram hydrobromide (5.5 g, 13.6 mmol) in 500 mL EtOAc was washed with dilute ammonium hydroxide (100 mL). The EtOAc layer was washed 3×100 mL saturated aqueous NaCl and dried with $MgSO_4$. The solvent was removed in vacuo and the residue was treated with 1-chlorethyl chloroformate (29.6 mL, 27.2 mmol), heated to 130° C. for 6 hr, cooled to rt and concentrated in vacuo. The residue was dissolved with 150 mL $CH_3OH$ and heated for 5 hr at 65° C. The solvents were then removed in vacuo. The crude product was dissolved in THF (50 mL) and 50 mL of 1N NaOH were added. The mixture was stirred at rt for an additional 14 hr, then extracted with EtOAc (3×50 mL). The extracts were washed with saturated NaCl (3×100 mL), dried with $Na_2SO_4$ and the solvents removed. Chromatography on silica gel, eluting with a gradient (100% $CH_2Cl_2$ to 50% $CH_3OH$: 50% $CH_2Cl_2$) gave the product as a clear oil, 3.102 g (74%).

Example 1

N-{3-[5-cyano-1-(4-fluorophenyl)-1,3-dihydro-2-benzofuran-1-yl]propyl}-N-methyl-ethanimidamide

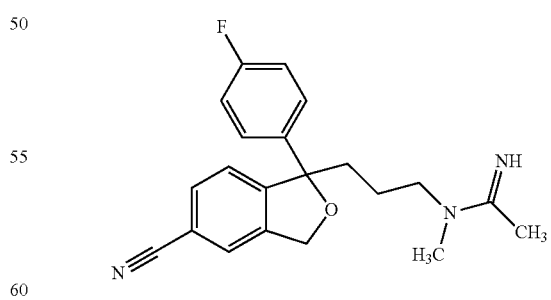

1-[3-(methylamino)propyl]-1-(4-fluorophenyl)-1,3-dihydro-2-benzofuran-5-carbonitrile (1.00 g, 3.22 mmol), the title compound from Preparation 1, and methyl ethanimidoate (0.283 g, 3.87 mmol, 1.2 equiv.) were dissolved in 1.9 mL of toluene and heated to 80° C. for 14 hr under $N_2$. The reaction was concentrated in vacuo to remove the toluene. The crude product was purified by liquid chromatography to give the title compound, 0.450 g (40%), as a light yellow semisolid.

LC: 93.1%;

MS: calcd. for $C_{21}H_{22}FN_3O$: 351.43, obsd. 351.17 ($M^+$).

$^1$H-NMR (DMSO-$d_6$, 400 MHz, T=36° C.) δ 1.16-1.46 (dm, 2H), 1.90 (s, 3H, C—C$\underline{H}_3$), 2.15 (m, 2H), 2.70 (s, 3H, N—C$\underline{H}_3$), 3.18 (t, 2H), 5.18 (q, 2H), 6.30 (bs, 1H, =N$\underline{H}$), 7.15 (t, 2H), 7.58 (m, 2H), 7.76 (m, 3H).

Example 2

N-{3-[5-cyano-1-(4-fluorophenyl)-1,3-dihydro-2-benzofuran-1-yl]propyl}-N-methyl-phenylmethanimidamide

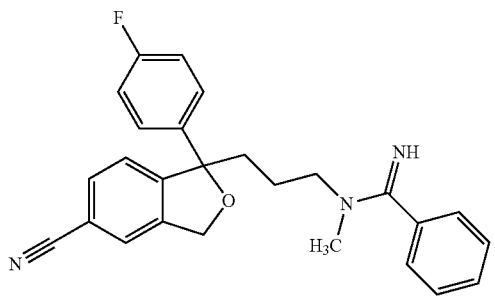 [SMILES: CN(CCCC1(c2ccc(F)cc2)OCc2cc(C#N)ccc21)C(=N)c1ccccc1]

A mixture of 0.350 g (1.13 mmol) of 1-[3-(methylamino)propyl]-1-(4-fluorophenyl)-1,3-dihydro-2-benzofuran-5-carbonitrile (Preparation 1) and methyl benzenecarboximidoate hydrochloride (0.213 g, 1.24 mmol, 1.1 equiv.) in 0.7 mL of N-methyl-pyrrolidinone was treated with potassium carbonate (0.11 g, 0.79 mmol, 0.7 equiv.) and heated to 80° C. for 15 hr. The solvent was then removed and the crude product purified by column chromatography to give the title compound 0.096 g (19%) as a white solid.

LC: 95.4%;

MS: calcd. for $C_{26}H_{24}FN_3O$: 413.50, obsd. 413.19 ($M^+$).

$^1$H-NMR (DMSO-$d_6$, 400 MHz, T=30° C.) δ 1.35 (m, 1H), 1.60 (dm, 1H), 2.0 (m, 1H), 2.30 (t, 1H), 2.85 (s, 1H), 3.15-3.25 (t, 2H), 3.55 (t, 1H), 5.05 (q, 1H), 5.20 (q, 1H), 7.15 (m, 2H), 7.37-7.90 (m, 10H), 8.9-9.4 (m, 2H).

Example 3

1-(4-fluorophenyl)-1-{3-[methyl(3,4,5,6-tetrahydropyridin-2-yl)amino]propyl}-1,3-dihydro-2-benzofuran-5-carbonitrile

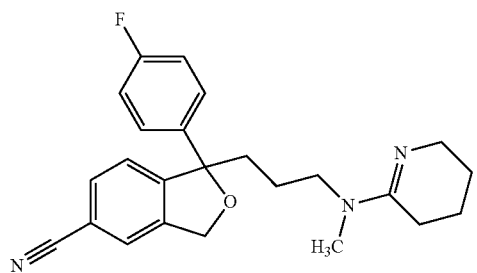 [SMILES: CN(CCCC1(c2ccc(F)cc2)OCc2cc(C#N)ccc21)C1=NCCCC1]

A mixture of 0.200 g (0.64 mmol) of 1-[3-(methylamino)propyl]-1-(4-fluorophenyl)-1,3-dihydro-2-benzofuran-5-carbonitrile (Preparation 1) and 6-methoxy-2,3,4,5-tetrahydropyridine (0.080 g, 0.71 mmol, 1.1 equiv.) was heated at 80° C. for 15 hr, cooled to rt and concentrated in vacuo to a gummy residue. The crude product was purified using column chromatography to give the title product as an off-white solid, 0.060 g (24%).

LC: 97.1%;

MS: calcd. for $C_{24}H_{26}FN_3O$: 391.49, obsd. 391.21 ($M^+$).

$^1$H-NMR (DMSO-$d_6$, 400 MHz, T=30° C.) δ 1.23-1.52 (dm, 2H), 1.67 (m, 4H), 2.20 (m, 2H), 2.92 (s, 3H, —N—CH3), 3.20-3.45 (dt, 4H), 3.57 (s, 2H), 5.18 (q, 2H), 7.15 (t, 2H), 7.58 (m, 2H), 7.80 (m, 3H).

Determination of Biological Activity

T. brucei brucei Assay

The growth inhibition assay for T. brucei brucei was conducted as described previously by Z. B. Mackey et al (Kenny K. H. Ang, Joseline Ratnam, Jiri Gut, Jennifer Legac, Elizabeth Hansell, Zachary B. Mackey, Katarzyna M. Skrzypczynska, Anjan Debnath, Juan C. Engel, Philip J. Rosenthal, James H. McKerrow, Michelle R. Arkin, Adam R. Renslo (2011) "Mining a Cathepsin Inhibitor Library for New Antiparasitic Drug Leads", PLoS Neglected Tropical Diseases, 5(5):e1023). Bloodstream forms of the monomorphic T. brucei brucei clone 427-221a were grown in complete HMI-9 medium containing 10% FBS, 10% Serum Plus medium (Sigma Inc., St. Louis, Mo., USA), 50 U/mL penicillin and 50 mg/mL streptomycin (Invitrogen) at 37° C. under a humidified atmosphere and 5% $CO_2$. Inhibitor stocks were prepared in 100% DMSO and screened at 5 mM for percent inhibition values or serially diluted from 25 mM to 0.04 mM in 10% DMSO for 1050 determinations. 5 mL of each dilution was added to 95 mL of diluted parasites (16104 cells per well) in sterile Greiner 96-well flat white opaque culture plates such that the final DMSO concentration was 0.5%. The 0% inhibition control wells contained 0.5% DMSO while 100% inhibition control wells contained 50 mM thimerosal (Sigma). After compound addition, plates were incubated for 40 hours at 37° C. At the end of the incubation period, 50 mL of CellTiter-Glo™ reagent (Promega Inc., Madison, Wis., USA) was added to each well and plates were placed on an orbital shaker at room temperature for 2 min to induce lysis. After an additional 10 min of incubation without shaking to stabilize the signal, the ATP-bioluminescence of each well was determined using an Analyst HT plate reader (Molecular Devices, Sunnyvale, Calif., USA). Raw values were converted to log 10 and percentage inhibition calculated relative to the controls. IC50 curve fittings were performed with Prism 4 software as above. Pentamidine was used as a comparator in the assay.

| Data | |
|---|---|
| Compound Example | IC50 (μM) (95% Confidence Intervals) |
| 1 | 10 |
| 2 | 1.1 |
| 3 | 20 |

The invention claimed is:
1. A compound of the formula I:

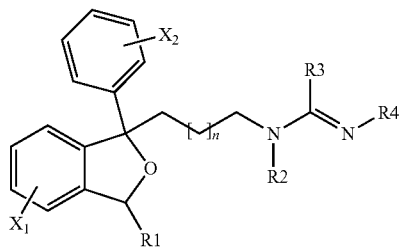

or the pharmaceutically acceptable salt(s) thereof, wherein:
$X_1$ is selected from the group consisting of H, $(C_1-C_4)$-alkyl, $(C_1-C_4)$-alkoxyl, $CF_3$, F, Cl, Br, I and CN;
$X_2$ is H, I, Br, Cl, or F;
n is zero, one or two;
R1 is H, methyl, or dimethyl;
R2 is H, $(C_1-C_6)$-alkyl;
R3 is H, $(C_1-C_6)$-alkyl, $(C_3-C_{12})$-cycloalkyl (optionally containing a S or O atom), aryl (optionally substituted by $X_3$), or $((C_1-C_6)$-alkyl)-aryl;
R4 is $(C_1-C_6)$-alkyl, aryl (optionally substituted by $X_4$); or
R3 and R4 together with the atoms to which they are attached form a 5-12 member mono- or bi-cyclic ring system, said ring system containing up to two additional heteroatoms selected from N, O or S and said ring optionally substituted at available positions by one or more groups selected from $(C_1-C_6)$-alkyl, $(C_1-C_6)$-alkoxyl and aryl;
$X_3$ and $X_4$ are independently selected from the list consisting of: H, F, Cl, Br, I, CN, $(C_1-C_6)$alkyl, $(C_3-C_{12})$ cycloalkyl, $CF_3$, $C_2F_5$, $OCF_3$, O—$(C_1-C_6)$-alkyl, O—$(C_1-C_6)$-alkoxyl, OH, $NO_2$, $NH_2$, NHR7 and NR7R8; wherein R7 and R8 are independently selected from the list consisting of $(C_1-C_6)$-alkyl, $(C_3-C_{12})$-cycloalkyl and phenyl, or wherein R7 and R8 together with the N to which they are attached form a 4-12 membered mono- or bi-cyclic ring.
2. The compound of claim 1, wherein R1 is hydrogen.
3. The compound of claim 1, wherein $X_1$ is 5-cyano.
4. The compound of claim 1, wherein $X_2$ is 4-fluoro.
5. The compound of claim 1, wherein n is one.
6. The compound of claim 1, wherein R2 is methyl.
7. The compound of claim 1, wherein R4 is hydrogen.
8. The compound of claim 1, wherein R3 and R4, taken together with the carbon and nitrogen atoms, respectively, to which they are attached form a 5-12 member mono or bicyclic ring system.
9. The compound of claim 1, wherein R3 and R4, taken together with the carbon and nitrogen atoms, respectively, to which they are attached form a group selected from
4,5-dihydro-imidazol-2-yl; 1,3,4-oxadiazol-2-yl, 1,2,4-triazol-3-yl, tetrazole-5-yl, 3,4-dihydro-quinolin-2-yl; 3,4-dihydro-2H-pyrrol-5-yl; 2,3,4,5-tetrahydro-pyridin-6-yl; 1,2,3,6-tetrahydro-pyrazin-2-yl; 3,6-dihydro-2H-1,4-oxazin-5-yl; 1,2-dihydro-quinoxalin-3-yl; 4,5-dihydro-3H-2-benzazepin-1-yl; and 2,5-dihydro-1H-3-benzazepin-4-yl.
10. The compound of claim 1, wherein R1 is hydrogen, R2 is methyl, R3 is hydrogen, n is one, X1 is cyano, and $X_2$ is 4-fluoro.

11. A compound of formula I according to claim 1, wherein the compound is selected from:
N-{3-[5-cyano-1-(4-fluorophenyl)-1,3-dihydro-2-benzofuran-1-yl]propyl}-N-methyl-ethanimidamide; and
N-{3-[5-cyano-1-(4-fluorophenyl)-1,3-dihydro-2-benzofuran-1-yl]propyl}-N-methyl-phenylmethanimidamide.

12. The compound of formula I according to claim 1, wherein the compound is selected from the group consisting of:
1-(4-fluorophenyl)-1-{3-[methyl(3,4,5,6-tetrahydropyridin-2-yl)amino]propyl}-1,3-dihydro-2-benzo-furan-5-carbonitrile;
1-{3-[3,4-dihydro-2H-pyrrol-5-yl(methyl)amino]propyl}-1-(4-fluorophenyl)-1,3-dihydro-2-benzofuran-5-carbonitrile;
1-{3-[3H-indol-2-yl(methyl)amino]propyl}-1-(4-fluorophenyl)-1,3-dihydro-2-benzo-furan-5-carbonitrile;
1-{3-[3,4-dihydroquinolin-2-yl(methyl)amino]propyl}-1-(4-fluorophenyl)-1,3-dihydro-2-benzofuran-5-carbonitrile;
1-{3-[3,4,4a,5,6,7,8,8a-octahydroquinolin-2-yl(methyl)amino]propyl}-1-(4-fluorophenyl)-1,3-dihydro-2-benzofuran-5-carbonitrile;
1-{3-[methyl(4-methyl-3,4,5,6-tetrahydropyrazin-2-yl)amino]propyl}-1-(4-fluorophenyl)-1,3-dihydro-2-benzofuran-5-carbonitrile;
1-{3-[5,6-dihydro-2H-1,4-oxazin-3-yl(methyl)amino]propyl}-1-(4-fluorophenyl)-1,3-dihydro-2-benzofuran-5-carbonitrile;
1-{3-[5,6-dihydro-2H-1,4-thiazin-3-yl(methyl)amino]propyl}-1-(4-fluorophenyl)-1,3-dihydro-2-benzofuran-5-carbonitrile;
1-{3-[methyl(2,3,6,7-tetrahydro-1,4-oxazepin-5-yl)amino]propyl}-1-(4-fluorophenyl)-1,3-dihydro-2-benzofuran-5-carbonitrile;
1-{3-[methyl(3,4,5,6-tetrahydro-2H-azepin-7-yl)amino]propyl}-1-(4-fluorophenyl)-1,3-dihydro-2-benzofuran-5-carbonitrile;
1-{3-[(2,2-dimethyl-3,4-dihydro-2H-pyrrol-5-yl)(methyl)amino]propyl}-1-(4-fluorophenyl)-1,3-dihydro-2-benzofuran-5-carbonitrile;
1-{3-[methyl(4H-1,2,3-triazol-5-yl)amino]propyl}-1-(4-fluorophenyl)-1,3-dihydro-2-benzo-furan-5-carbonitrile;
N-3-(5-cyano-1-(4-fluorophenyl)-1,3-dihydro-2-benzofuran-1-yl)-propyl]-N-methyl-propanimidamide;
N-3-(5-cyano-1-(4-fluorophenyl)-1,3-dihydro-2-benzofuran-1-yl)-propyl]-N-methyl-cyclopropanecarboximidamide
N-3-(5-cyano-1-(4-fluorophenyl)-1,3-dihydro-2-benzofuran-1-yl)-propyl]-N-methyl-cyclohexanecarboximidamide
N-3-(5-cyano-1-(4-fluorophenyl)-1,3-dihydro-2-benzofuran-1-yl)-propyl]-N-methyl-tetrahydro-2H-pyran-4-carboximidamide;
N-3-(5-cyano-1-(4-fluorophenyl)-1,3-dihydro-2-benzofuran-1-yl)-propyl]-4-chloro-N-methylbenzenecarboximidamide;
N-3-(5-cyano-1-(4-fluorophenyl)-1,3-dihydro-2-benzofuran-1-yl)-propyl]-3,4-difluoro-N-methylbenzenecarboximidamide;

N-3-(5-cyano-1-(4-fluorophenyl)-1,3-dihydro-2-benzofuran-1-yl)-propyl]-4-methoxy-N-methylbenzenecarboximidamide;

N-3-(5-cyano-1-(4-fluorophenyl)-1,3-dihydro-2-benzofuran-1-yl)-propyl]-N-methyl-naphthalene-2-carboximidamide;

N-3-(5-cyano-1-(4-fluorophenyl)-1,3-dihydro-2-benzofuran-1-yl)-propyl]-N-methyl-naphthalene-1-carboximidamide;

(1Z)—N-3-(5-cyano-1-(4-fluorophenyl)-1,3-dihydro-2-benzofuran-1-yl)-propyl]-N,N'-dimethylethanimidamide;

(1E)-N-3-(5-cyano-1-(4-fluorophenyl)-1,3-dihydro-2-benzofuran-1-yl)-propyl]-N,N'-dimethylethanimidamide;

(1Z)—N-3-(5-cyano-1-(4-fluorophenyl)-1,3-dihydro-2-benzofuran-1-yl)-propyl]-N,N',2-trimethylpropanimidamide;

(1Z)—N-3-(5-cyano-1-(4-fluorophenyl)-1,3-dihydro-2-benzofuran-1-yl)-propyl]-N,N'-dimethyl-3-phenylpropanimidamide;

N-3-(5-cyano-1-(4-fluorophenyl)-1,3-dihydro-2-benzofuran-1-yl)-propyl]-N,N'-dimethyl-benzenecarboximidamide;

1-{-3-[4,5-dihydro-1H-3-benzazepin-2-yl-amino]propyl}-1-(4-fluorophenyl)-1,3-dihydro-2-benzofuran-5-carbonitrile;

1-{3-[4,5-dihydro-3H-2-benzazepin-1-yl-amino]propyl}-1-(4-fluorophenyl)-1,3-dihydro-2-benzofuran-5-carbonitrile; and 1-{3-[4-methyl-3,4-dihydroquinoxalin-2-yl(methyl)amino]propyl}-1-(4-fluorophenyl)-1,3-dihydro-2-benzofuran-5-carbonitrile.

13. A pharmaceutical composition comprising a compound of formula I according to claim 1, or a pharmaceutically acceptable salt thereof, and a pharmaceutically acceptable carrier.

14. A method of treatment of a mammal having human African trypanosomiasis, malaria, Chagas disease, or Leishmaniasis, the method comprising administering to said mammal a compound of formula I according to claim 1, or a pharmaceutically acceptable salt thereof.

15. The method of claim 14, wherein the mammal is a human.

\* \* \* \* \*